Figure 1:
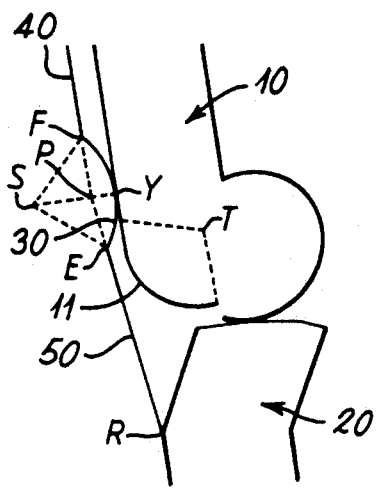

United States Patent [19]

Goodfellow et al.

[11] Patent Number: 5,246,460
[45] Date of Patent: Sep. 21, 1993

[54] PROSTHETIC PATELLAR COMPONENTS

[75] Inventors: John W. Goodfellow, Woodeaton; John J. O'Connor, Headington, both of England

[73] Assignee: British Technology Group Ltd., London, England

[21] Appl. No.: 849,053

[22] PCT Filed: Aug. 28, 1991

[86] PCT No.: PCT/GB91/01447

§ 371 Date: Apr. 27, 1992

§ 102(e) Date: Apr. 27, 1992

[87] PCT Pub. No.: WO92/03109

PCT Pub. Date: Mar. 5, 1992

[30] Foreign Application Priority Data

Aug. 28, 1990 [GB] United Kingdom ............... 9018737

[51] Int. Cl.$^5$ ............................................. A61F 2/38
[52] U.S. Cl. .................................................... 623/20
[58] Field of Search ........................... 623/16, 18, 20

[56] References Cited

U.S. PATENT DOCUMENTS

| 3,964,106 | 6/1976 | Hutter et al. | 623/20 |
| 4,007,495 | 2/1977 | Frazier | 623/20 |
| 4,085,466 | 4/1978 | Goodfellow et al. | 623/20 |
| 4,634,444 | 1/1987 | Noiles | 623/20 |

FOREIGN PATENT DOCUMENTS

| 1534263 | 11/1978 | European Pat. Off. | 623/20 |
| 8325767 | 9/1983 | Fed. Rep. of Germany | 623/20 |
| WO85/03425 | 8/1985 | PCT Int'l Appl. | 623/20 |
| 2215610A | 2/1989 | United Kingdom | 623/20 |

Primary Examiner—David Isabella
Attorney, Agent, or Firm—Cushman, Darby & Cushman

[57] ABSTRACT

A prosthetic patellar component is provided which has a fixation part adapted to be secured to the bone of the patella and an articulation part defining a surface for replacing the femoral facet of the natural patella, with these parts being mutually engageable in such a manner as to allow rotation between them about a medio-lateral axis relative to the surface which replaces the femoral facet.

5 Claims, 1 Drawing Sheet

PROSTHETIC PATELLAR COMPONENTS

This invention concerns prosthetic components for replacement of the femoral facet of the patella.

Components of this kind have been in routine use for some years, typically, although not exclusively, for total knee joint replacement in association with other components to replace the patellar and tibial facets of the distal femur and also the femoral facets of the proximal tibia. However there is a current concern with the rates of failure found to arise with such components due to component wear and other causes, and this applies not least of all to patellar components.

The cause of these failure rates can be explained, at least in part, by a new analysis of the knee joint which is expressed in a paper entitled "Kinematics and Mechanics of the Cruciate Ligaments of the Knee" by O'Connor J. J. and Zavatsky A. presented at the First World Congress on Biomechanics, Symposium of Biomechanics of Biarthrodial Joints, San Diego, Calif., 1990. This paper is now published as Chapter 25 in the related proceedings, Vol. 2, pages 197-252, edited by V. C. Mow, A. Ratcliffe and S. L.-Y. Woo, Springer-Verlag, New York, 1990. In any event, this analysis is thought to be consistent with the natural function of the knee joint as so far observed and understood, patellar components as previously used to date are not adequately consistent with the analysis, and the failure rates so far as patellar components are concerned can be explained as a result of this inconsistency.

An object of the present invention is accordingly to provide a prosthetic patellar component which is more consistent with the analysis in question and, to this end, such a component comprises a fixation part adapted for securement to the bone of a patella, and an articulation part defining a surface to assume the role of the femoral facet of that patella, said parts being mutually engageable in such a manner as to allow rotation therebetween about a medio-lateral axis relative to said surface.

Figure 2:
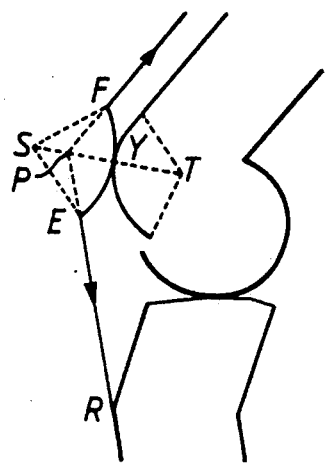
Figure 3:
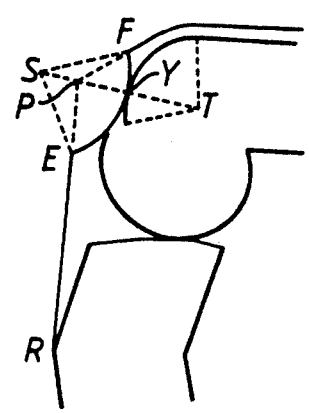
Figure 4:
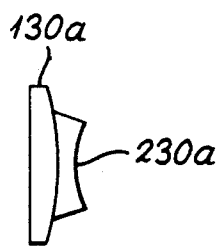
Figure 5:
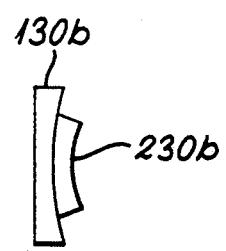

In order to clarify the nature of the proposed component and the analysis on which it is based, the same are further described below with reference to the accompanying drawings, in which:

FIGS. 1-3 diagrammatically illustrate, in a sagittal plane and respectively different positions of flexion-extension, a model of the knee joint on which the analysis is based, and FIGS. 4 and 5 similarly illustrate respectively different forms of component according to the invention.

In FIGS. 1-3 the joint model is respectively at full extension, 50° flexion and 100° flexion.

The distal femur is denoted at 10 and the proximal tibia at 20. The patella is denoted at 30 by way of a circular arc representing the femoral facet, this arc being centred at S and engaged with the femur at Y. This engagement is located just beyond the proximal extremity of the trochlea at full extension as seen in FIG. 1, the trochlea being denoted at 11 as a circular arc centred at T, with the engagement progressing distally around the trochlea with flexion movement as seen from FIGS. 2 and 3.

The remaining structural elements of direct interest in FIGS. 1-3 are the quadriceps tendon which is denoted at 40 and connected to the patella at F, and the patellar tendon which is denoted at 50 and connected at its opposite ends respectively to the patella and tibia at E and R.

According to the analysis under consideration, determination of the spatial position of the patella and its engagement with the femur must satisfy the geometrical conditions that the point E remains at a constant distance from R, that point Y lies on the line from centre S which is perpendicular to the femur, and that the quadriceps tendon remains substantially parallel to the femur over which it passes. However, these conditions are not sufficiently determinative and it is additionally appropriate to apply the mechanical condition that the lines of action of the forces on the patella intersect. For this purpose the lines of action of the forces in the two tendons should intersect on the line of action SY of the patello-femoral force and this point of intersection is denoted at P.

The result of these conditions in terms of patella position is that not only does the point Y move distally and posteriorly on the femur as is to be expected, but the point Y also moves proximally on the patella during flexion. This last movement involves rotation of the patella about a medio-lateral axis and is essentially a consequence of the mechanical condition.

Generally speaking prior patellar components are of fixed geometry, or at least have no in-built capability for rotation about a medio-lateral axis, and so can only rotate in this way together with the remnant patellas with which they are secured. Accordingly, like the natural patella, such components will have a varying engagement with the femur and, because this component engagement is of a direct nature in the absence of any intervening soft tissue, the engagement is effectively of line or point form with a consequent tendency to rapid wear. In this connection it will be understood that any attempt to provide a more congruous engagement for this purpose by appropriate choice of surface geometry will inevitably impact adversely on the ability of the component to slide and rotate in a congruent manner relative to the femur as the engagement point Y moves along and round the same during flexion-extension.

The present invention alleviates this situation by providing, in effect, a patellar component of two-part form as between fixation and articulation parts with an interface between the two parts allowing rotation about a medio-lateral axis. In use of such a component the fixation part can rotate with the remnant patella to meet the mechanical condition, with the patello-femoral force being applied by way of the articulation part, but without this last part needing to rotate for this purpose. The femoral facet surface of the articulation part will accordingly be more consistent in its engagement with the femur and is open to greater freedom of geometry in its design to provide increased congruity in this engagement.

The two parts of the component preferably interface in generally concave manner relative to the facet surface, but may also interface convexly, as respectively shown in FIGS. 4 and 5 in order to provide the desired rotation capability. As a result of this capability the femoral facet can be concave as seen sagittally in these figures, in which the fixation and articulation parts are denoted respectively at 130 and 230, with the parts distinguished by the addition of a in FIG. 4 and b in FIG. 5. Parts 130 and 230 will typically be respectively of metal and plastics material for use in association with a metal femoral component.

Also the curvature of the interface geometry may only extend in a single dimension, but it is preferably of effectively spherical form to extend in two dimensions. While singly curved geometry interfacing is adequate, it will require securement of the component in a particular orientation. Also the provision of spherical interfacing will allow rotation other than about a medio-lateral axis and this will better accommodate the component to take account of other rotations in the knee joint function, such as that which occurs about the long axis of the joint through the femur and tibia during flexion-extension.

In addition, while not essential to the extent that it is held between the fixation part and femur during use, the articulation part of the proposed component can be rendered captive with the associated fixation part or otherwise restricted in the extent of its movement relative to the latter, to obviate or reduce the risk of dislocation. Suitable arrangements for this purpose can be similar to those proposed previously for use in prosthetic knee joint devices involving so-called meniscal components and according generally with Patent Specification No. GB 1534263/U.S. Pat. No. 4,085,466.

Adaption of the fixation parts for securement with bone can be of any suitable form.

We claim:

1. In a human knee joint, an implantable prosthetic patellar component comprising a first part sized to be fixed to the bone of the patella, and a second part defining an articulation surface which replaces the natural femoral facet of the patella, said first and second parts being mutually engaged in such a manner as to allow rotation therebetween about a medio-lateral axis of the joint.

2. A component according to claim 1 wherein said first part has a first curved interface surface opposite to said bone, said second part has a second curved interface surface opposite to said articulation surface and said first and second interface surfaces are mutually slidably engaged to allow said rotation.

3. A component according to claim 1 wherein said first and second interface surfaces are respectively convexly and concavely curved.

4. A component according to claim 3 wherein said first and second interface surfaces are each spherically shaped.

5. A component according to any one of claims 1, 2, 3 or 4 wherein said articulation surface has a concave sagittal profile.

* * * * *